United States Patent [19]

Van Der Puy et al.

[11] Patent Number: 4,968,803
[45] Date of Patent: Nov. 6, 1990

[54] PROCESS FOR THE PREPARATION OF 2-HYDROXYPYRIDINE OR QUINOLINE COMPOUNDS

[75] Inventors: Michael Van Der Puy, Cheektowaga; David Nalewajek, West Seneca, both of N.Y.; Gene Wicks, Baton Rouge, La.

[73] Assignee: Allied-Signal Inc., Morristown, N.J.

[21] Appl. No.: 335,244

[22] Filed: Apr. 10, 1989

[51] Int. Cl.$^5$ .......................................... C07D 213/803
[52] U.S. Cl. .................................... 546/156; 546/170; 546/298; 546/299
[58] Field of Search ................. 546/156, 170, 298, 299

[56] References Cited

U.S. PATENT DOCUMENTS

| | | | |
|---|---|---|---|
| 3,691,171 | 9/1972 | Boosen | 546/156 |
| 4,496,733 | 1/1985 | Quarroz | 546/310 |
| 4,556,716 | 12/1985 | Quarroz | 546/345 |
| 4,786,733 | 11/1988 | Van Der Puy et al. | 546/286 |
| 4,797,149 | 1/1989 | Lee et al. | 71/94 |
| 4,797,409 | 1/1989 | Lohaus et al. | 514/345 |
| 4,801,716 | 1/1989 | Sharvit et al. | 546/345 |
| 4,816,588 | 3/1989 | Rieker et al. | 546/321 |
| 4,849,519 | 7/1989 | Maurer | 546/298 |
| 4,849,523 | 7/1989 | Kelly | 546/345 |

FOREIGN PATENT DOCUMENTS

225172  6/1987  European Pat. Off. ............ 546/298

OTHER PUBLICATIONS

S. Rozen et al., J. Org. Chem. 53, 1123 (1988).
M. Van Der Puy, Tetrahedron Letters 28(3), 255 (1987).
M. Van Der Puy et al., Terahedron Letters, vol. 29, No. 35, pp. 4389–4392 (1988).
Watanabe et al., Bull. Chem. Soc. Jpn. 54, 127 (1981).
S. Rozen et al., Angew Chem. Int. Ed. Engl. 25(6), 554 (1986).
S. Rozen et al., J. Am. Chem. Soc. 109, 3789 (1987).
T. Umemoto et al., Tetrahedron Letters 28 (24), 2705 (1987).
Research Disclosure 24016 (1984).
H. L. Bradlow et al., J. Org. Chem. 14, 509 (1949).
E. Spinner et al., J. Chem. Soc. (B), 289 (1971).
W. T. Caldwell et al., J. Am. Chem. Soc. 66, 1479 (1944).
J. Fried et al., J. Org. Chem. 6, 566 (1941).

*Primary Examiner*—John M. Ford
*Assistant Examiner*—Jacqueline Haley
*Attorney, Agent, or Firm*—Melanie L. Brown; Jay P. Friedenson

[57] ABSTRACT

The present invention relates to a process for the preparation of hydroxypyridine based compounds. The process comprises the step of: in water, reacting a pyridine based compound with the proviso that the second position on the nitrogen ring is unsubstituted and the fourth position in the nitrogen ring is not substituted with halogen, with elemental fluorine at a temperature of about −25° to about +30° C. for a time sufficient to form a 2-hydroxypyridine based compound.

The resulting 2-hydroxypyridine or quinoline carboxylic acids and esters are useful as herbicide and pharmaceutical intermediates.

20 Claims, No Drawings

PROCESS FOR THE PREPARATION OF 2-HYDROXYPYRIDINE OR QUINOLINE COMPOUNDS

BACKGROUND OF THE INVENTION

The present invention relates to a process for the preparation of 2-hydroxypyridine or quinoline compounds and more particularly 2-hydroxypyridine or quinoline carboxylic acids and esters.

2-Hydroxypyridine or quinoline carboxylic acids and esters are useful as herbicide and pharmaceutical intermediates. One method for their preparation involves oxidizing quinolinic acid to obtain 2 3-bis(methoxycarbonyl)pyridine N-oxide, treating the N-oxide with acetic anhydride to give the 2-acetoxy compound, and hydrolyzing to give 6-hydroxy-2,3-dimethoxycarboxylpyridine in 27.5% overall yield; see E. Spinner et al., J. Chem. Soc. (B), 289 (1971). Another method involves reacting an ester of coumalic acid with ammonia to yield 2-hydroxy-5-pyridinecarboxylic acid; see W. T. Caldwell et al. J. Am. Chem. Soc. 66, 1479 (1944). Another method involves converting alpha-pyrone-6-carboxylic acid with ammonium acetate and glacial acetic acid into 2-pyridine-6-carboxylic acid; see J. Fried et al., J. Org. Chem. 6, 566 (1941).

Unsubstituted 2-hydroxypyridines may be prepared in several ways. T. Umemoto et al., Tetrahedron Letters 28(24), 2705 (1987) teach reacting N-fluoropyridinium triflate with alkaline solution to give 50% 2-hydroxypyridine. Research Disclosure 24016 (1984) teaches contacting a 3,4-dihydro-2-pyridone with a catalytic amount of a Group VIII metal on a support in a suitable solvent at elevated temperatures to produce 2-pyridinols. Another method consists of a 3-step sequence involving oxidation of a pyridine compound with a peracid to give a pyridine-N-oxide, followed by treatment of the N-oxide with $PCl_5$ to give the corresponding 2-chloropyridine, and finally hydrolysis to the pyridinol. See H. L. Bradlow et al., J. Org. Chem. 14 509 (1949).

N-Oxides of 2-pyridine carboxylic acids react with tertiary amines and acetic anhydride in the presence of halogen-producing compounds to yield 2-halopyridine carboxylic acids as taught by U.S. Pat. No. 4,556,716 and in the presence of nitriles to yield 2-aminopyridine carboxylic acids as taught by U.S. Pat. No. 4,496,733. U.S. Pat. No. 4,797,149 teaches compounds such as ethyl 2,6-bis(trifluoromethyl)-4-hydroxy-3-pyridinecarboxylate. U.S. Pat. No. 4,801,716 teaches a process for the preparation of heptachloropicoline.

U.S. Pat. No. 4,797,409 teaches 1-hydroxy-2-pyridones which are prepared by reacting 6-halogenomethyl-2-pyrones with phenols and then converting the intermediate by reacting with hydroxylamine.

Elemental fluorine is a well known fluorinating agent but it has rarely been used as an oxidant to prepare nonfluorinated organic compounds; for examples, see N. Watanabe et al., Bull. Chem. Soc. Jpn. 54, 127 (1981) which teaches oxidizing alcohol to aldehyde with carbon impregnated with elemental fluorine and S. Rozen et al.. Angew Chem. Int. Ed. Engl. 25(6), 554 (1986) which teaches treating olefins in aqueous acetonitrile with elemental fluorine to give epoxides.

According to S. Rozen et al., J. Am Chem. Soc. 109, 3789 (1987) and S. Rozen et al., J. Org. Chem. 53, 1123 (1988), acetyl hypofluorite, which is a useful fluorinating agent, oxidizes pyridine to yield 2-acetoxypyridine. The article reports that an electron-withdrawing group at the 2-position inhibits the reaction Pyridine esters when treated with elemental fluorine in organic solvent yield the corresponding 2-fluoropyridines according to M. Van Der Puy, Tetrahedron Letters 28(3), 255 (1987) and U.S. Pat. No. 4,786,733.

Because they are useful as herbicide and pharmaceutical intermediates, a simple one-step process for the preparation of 2-hydroxypyridine or quinoline carboxylic acids and esters in high yield is needed.

SUMMARY OF THE INVENTION

The present invention provides a process for the preparation of 2-hydroxypyridine based compounds. The process comprises the step of: in water reacting a pyridine based compound with the proviso that the second position on the nitrogen ring is unsubstituted and the fourth position on the nitrogen ring is not substituted with halogen, with elemental fluorine at a temperature of about $-25°$ to about $+30°$ C. for a time sufficient to form a 2-hydroxypyridine based compound. The term "pyridine based compound" as used herein includes pyridine and quinoline compounds.

Unlike known processes for the preparation of 2-hydroxypyridine and quinoline carboxylic acids and esters, the present process provides these compounds in one step and a higher yield. Also in contrast to acetyl hypofluorite, which fails to react with pyridine having electron withdrawing groups at the second or sixth position on the nitrogen ring, the present process is operative even if the sixth position on the nitrogen ring is substituted with a strongly electron withdrawing group such as with picolinic acid and dimethyl pyridine-2,3-dicarboxylate.

Preferably, the process comprises the step of: reacting a compound of the Formula (I)

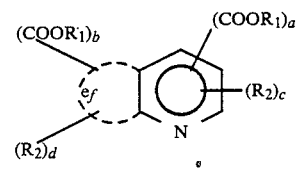

wherein $R_1$ is hydrogen, methyl or ethyl a and b are the same or different and the sum of a and b ranges from 1 to 6; $R_2$ is fluorine, chlorine, bromine or iodine; c and d are the same or different and the sum of c and d ranges from 0 to 5; $a+b+c+d \leq 6$; e represents the atoms necessary to form a six carbon ring; f is the number of additional six carbon rings and is 0 or 1; with the proViso that when $R_1$ is hydrogen, an alkali metal hydroxide is added to the water prior to the reaction and when $R_1$ is methyl or ethyl, a water-miscible organic solvent is added to the water prior to the reaction, and forms a 2-hydroxypyridine based compound of the Formula (II)

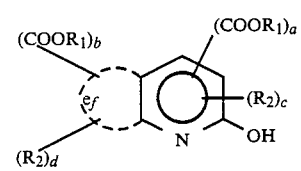

As such, the present invention fulfills the need in the art for a simple one-step process for the preparation of 2-hydroxypyridine or quinoline carboxylic acids and esters in high yield.

Other advantages of the present invention will become apparent from the following description and appended claims.

DETAILED DESCRIPTION OF THE PREFERRED EMBODIMENTS

Any pyridine based compound having functional groups which do not interfere with the reaction are useful in the present process, pyridine based compounds having a halogen at the fourth position on the nitrogen ring are generally unstable and as such, are not useful in the present process.

Some of the preferred starting compounds of Formula (I) are available in commercial quantities. The other compounds may be prepared by known methods such as those disclosed by U.S. Pat. No. 4,754,039.

Preferred pyridine monocarboxylic acids include isonicotinic acid; picolinic acid; nicotinic acid; 3-bromoisonicotinic acid; 3, 5-dichloroisonicotinic acid; 3,5,6-trifluoroisonicotinic acid; 3-bromopicolinic acid; 5-bromonicotinic acid; and 5,6-dichloronicotinic acid. Illustrative pyridine dicarboxylic acids include 2,3-pyridinedicarboxylic acid; 2,5-pyridinedicarboxylic acid; 3,4-pyridinedicarboxylic acid; 3,5-pyridinedicarboxylic acid; and 2,4-pyridinedicarboxylic acid. Other illustrative pyridine acids include 2,3,4-pyridinetricarboxylic acid; 2,3,5-pyridinetricarboxylic acid; 2,4,5-pyridinetricarboxylic acid; 3,4,5-pyridinetricarboxylic acid; 2,3,4,5-pyridinetetracarboxylic acid; and 5-bromo-2,3,4pyridinetricarboxylic acid.

Illustrative quinoline monocarboxylic acids include 3-quinolinecarboxylic acid; 4-quinolinecarboxylic acid; 5-quinolinecarboxylic acid; 6-quinolinecarboxylic acid; 7-quinolinecarboxylic acid; 8-quinolinecarboxylic acid; 3-chloro-4-quinolinecarboxylic acid; and 1-isoquinolinecarboxylic acid.

Illustrative quinoline dicarboxylic acids include 3,4-quinolinedicarboxylic acid; 3,5-quinolinedicarboxylic acid; 3,6-quinolinedicarboxylic acid; 3,7-quinolinedicarboxylic acid; 3,8-quinolinedicarboxylic acid; 4,5quinolinedicarboxylic acid; 4,6-quinolinedicarboxylic acid; 4,7-quinolinedicarboxylic acid; 4,8-quinolinedicarboxylic acid; 5,6-quinolinedicarboxylic acid; 5,7-quinolinedicarboxylic acid; 5,8-quinolinedicarboxylic acid ; 6,7-quinolinedicarboxylic acid; 6,8-quinolinedicarboxylic acid; and 5-bromo-3,4-quinolinedicarboxylic acid.

Illustrative quinoline tricarboxylic acids include 3,4,5-quinolinetricarboxylic acid; 3,4,6-quinolinetricarboxylic acid; 3,4,7-quinolinetricarboxylic acid; 3,4,8-quinolinetricarboxylic acid; 3,5,6-quinolinetricarboxylic acid; 3,5,7-quinolinetricarboxylic acid; 3,5,8-quinolinetricarboxylic acid; 3,6,7-quinolinetricarboxylic acid; 3,6,8-quinolinetricarboxylic acid; 3,7,8-quinolinetricarboxylic acid; 4,5,6-quinolinetricarboxylic acid; 4,5,7-quinolinetricarboxylic acid; 4,5,8-quinolinetricarboxylic acid; 4,6,7-quinolinetricarboxylic acid; 4,6,8-quinolinetricarboxylic acid; 4,7,8-quinolinetricarboxylic acid; 5,6,7-quinolinetricarboxylic acid; 5,6,8-quinolinetricarboxylic acid; 5,7,8-quinolinetricarboxylic acid; 6,7,8-quinolinetricarboxylic acid; 6-chloro-3,4,5-quinolinetricarboxylic acid; 5,7-difluoro-3,4,6-quinolinetricarboxylic acid; and 5,6,8-tribromo-3,4,7-quinolinetricarboxylic acid.

Illustrative quinoline tetracarboxylic acids include 3,4,5,6-quinolinetetracarboxylic acid; 3,4,5,7nolinetetracarboxylic acid; 3,4,5,8-quinolinetetracarboxylic acid; 3,5,6,7-quinolinetetracarboxylic acid; 3,5,6,8-quinolinetetracarboxylic acid; 3,5,7,8-quinolinetetracarboxylic acid; 3,6,7,8-quinolinetetracarboxylic acid; 4,5,6,7-quinolinetetracarboxylic acid; 4,5,6,8quinolinetetracarboxylic acid; 4,5,7,8-quinolinetetracarboxylic acid; 4,6,7,8-quinolinetetracarboxylic acid; 5,6,7,8-quinolinetetracarboxylic acid; 7-bromo-3,4,5,6quinolinetetracarboxylic acid; and 6,8-dichloro-3,4,5,7quinolinetetracarboxylic acid.

Illustrative quinoline pentacarboxylic acids include 3,4,5,6,7-quinolinepentacarboxylic acid; 3,4,5,6,8-quinolinepentacarboxylic acid; 3,4,5,7,8quinolinepentacarboxylic acid; 3,4,6,7,8-quinolinepentacarboxylic acid; 3,5,6,7,8-quinolinepentacarboxylic acid; 4,5,6,7,8-quinolinepentacarboxylic acid; 8-bromo-3,4,5,6 7-quinolinepentacarboxylic acid; and 3,4,5,6,7,8-quinolinehexacarboxylic acid.

Illustrative pyridine monoesters include methyl isonicotinate; ethyl isonicotinate; methyl picolinate; ethyl picolinate; methyl nicotinate; ethyl nicotinate; 3-bromo methyl isonicotinate; and 3,5-difluoro ethyl isonicotinate.

Preferred pyridine diesters include dimethyl pyridine-2,3-dicarboxylate; diethyl pyridine-2,3dicarboxylate; dimethyl pyridine-2,5-dicarboxylate; diethyl pyridine-2,5-dicarboxylate; dimethyl pyridine-3,4-dicarboxylate; diethyl pyridine-3,4-dicarboxylate; dimethyl pyridine-3,5-dicarboxylate; diethyl pyridine3,5-dicarboxylate; dimethyl pyridine-2,4-dicarboxylate; diethyl pyridine-2,4-dicarboxylate; and 5-fluorodimethyl pyridine-2,5-dicarboxylate. Other illustrative pyridine esters include trimethyl pyridine-2,3,4-tricarboxylate; triethyl pyridine-2,3,4-tricarboxylate; trimethyl pyridine-2,3,5-tricarboxylate; triethyl pyridine-2,3,5-tricarboxylate; trimethyl pyridine-2,4,5-tricarboxylate; triethyl pyridine-2,4 5-tricarboxylate; trimethyl pyridine-3,4,5-tricarboxylate; triethyl pyridine-3,4,5-tricarboxylate; tetramethyl pyridine-2,3,4,5-tetracarboxylate; tetraethyl pyridine-2,3,4,5-tetracarboxylate; and 5-fluoro trimethyl pyridine-2,3,4-tricarboxylate.

Preferred quinoline monoesters include methyl quinoline-3-carboxylate; ethyl quinoline-3-carboxylate; methyl quinoline-4-carboxylate; ethyl quinoline-4-carboxylate; methyl quinoline-5-carboxylate; ethyl quinoline-5-carboxylate; methyl quinoline-6-carboxylate; ethyl quinoline-6-carboxylate; methyl quinoline-7carboxylate; ethyl quinoline-7-carboxylate; methyl quinoline-8-carboxylate; ethyl quinoline-8-carboxylate; 3-bromo methyl quinoline-4-carboxylate; 3,5-dichloro methyl quinoline-4-carboxylate; 3,5,6-trifluoro methyl quinoline-4-carboxylate; 3,5,6,7-tetrabromo methyl quinoline-4-carboxylate; and 3,5,6,7,8-pentachloro methyl quinoline-4-carboxylate.

Illustrative quinoline diesters include dimethyl quinoline-3,4-dicarboxylate; diethyl quinoline-3,5-dicarboxylate; dimethyl quinoline-3,6-dicarboxylate; and diethyl quinoline-3,7-dicarboxylate. Illustrative quinoline triesters include trimethyl quinoline-3,4,5-tricarboxylate; triethyl quinoline-3,4,6-tricarboxylate; trimethyl quinoline-3,4,7-tricarboxylate; and triethyl quinoline-3,4,8-tricarboxylate. Other illustrative quinoline esters include tetramethyl quinoline-3,4,5,6tetracarboxylate; tetraethyl quinoline-3,4,5,7-tetracarboxylate; pentamethyl quinoline-3,4,5,6,7-pentacarboxylate; and pentaethyl quinoline-3,4,5,6,8-pentacarboxylate.

The most preferred compounds of the Formula (I) are isonicotinic acid, picolinic acid, nicotinic acid, dimethyl pyridine-2,3-dicarboxylate dimethyl pyridine-2,5-dicarboxylate, dimethyl pyridine-3,5-dicarboxylate, and methyl quinoline-4-carboxylate.

The pyridine based compound is added to water. The pyridine based compound should be soluble in water. As those skilled in the art will appreciate, the output of the process increases as the solubility of the pyridine based compound in water increases.

When the preferred starting compound of Formula (I) is an acid an alkali metal hydroxide is added to the water prior to the reaction so that the acid is in the form of its salt. Useful alkali metal hydroxides include potassium hydroxide and sodium hydroxide. Potassium hydroxide is preferred. These hydroxides are commercially available. About 1 to about 3 moles alkali metal hydroxide are added per mole —COOH group. The addition of alkali metal hydroxide also insures that the pyridine nitrogen is non-protonated during the reaction and helps to solubilize the acids.

The acid should be soluble in the water/hydroxide solution.

When the preferred starting compound of formula (I) is an ester, a water-miscible organic solvent is used because the esters typically have low water solubility. A useful water-miscible organic solvent is acetonitrile which is preferred. The ratio of organic solvent to water is about 1:1 to about 4:1 and is determined by the solubility of the ester in the water/solvent mixture.

The ester should be soluble in the water/solvent mixture.

After dissolving the acid in the water/hydroxide solution or the ester in the water/solvent mixture, elemental fluorine is bubbled into the stirred mixture. Preferably, the fluorine is bubbled for about 20 minutes to about 4 hours into the stirred mixture. Preferably, the elemental fluorine is diluted with nitrogen for safety reasons and to moderate the reaction. Preferably, about 5 to about 25% fluorine in nitrogen is used and most preferably about 5 to about 10% is used.

The solution temperature is about $-25°$ to about $30°$ C. Preferably, the temperature is about $0°$ to about $30°$ C. The use of lower temperatures is impractical because the pyridine compounds become insoluble. The use of higher temperatures is undesirable because undesirable side products result.

When the starting compound is an acid and excess alkali metal hydroxide is used, the product is in the ion form. The ion may be converted to the acid to facilitate extraction or to render it insoluble so that it can be filtered. This is accomplished by lowering the pH after the reaction. Concentrated hydrochloric acid may be used for this purpose.

The acid or ester product is then filtered from the reaction mixture and purified by recrystallization.

It should be understood that the products may exist in tautomeric pyridone form. All such tautomers are included within the products of the present process.

It should be understood that the 2-hydroxypyridine compounds were not formed by hydrolysis of the corresponding 2-fluoropyridines. After the present process, 2-fluoropyridine acids or esters could not be detected by nuclear magnetic resonance. While 2-fluoro-4-carbomethoxypyridine could not be detected following fluorination of methyl isonicotinate in water/acetonitrile fluorination of methyl isonicotinate mixed with 2-fluoro-4-carbomethoxypyridine resulted in methyl 2-hydroxyisonicotinate and unreacted methyl 2-fluoroisonicotinate.

The present invention was first described in our paper, M. Van Der Puy et al., "Controlled Regiospecific Oxidation of Pyridine Carboxylic Acids and Esters with Elemental Fluorine", *Tetrahedron Letters* 29 (35), 4389 (September 1988).

Based on the results obtained, the present process for the preparation of 2-pyridones from the corresponding pyridine compounds is a controlled, regiospecific transformation of C—H to C—OH in one step using $F_2$ as the primary oxidant.

The present invention is more fully illustrated by the following non-limiting Examples.

EXAMPLE 1

This Example is directed to the preparation of 2-hydroxyisonicotinic acid (2-hydroxypyridine-4-carboxylic acid).

Isonicotinic acid (5g) was dissolved in 50 mL water containing 6.7 g KOH. A mixture of $F_2$ in $N_2$ ($F_2$ at 10 cc/min., $N_2$ at 90 cc/min.) was bubbled into the mixture at ice-bath temperature for a total of 3.5 hours. The pH of the solution at this time was about 6. After warming to room temperature, the resultant liquid-solid mixture was treated with 3 mL conc. HCl, and stirred overnight. The mixture was filtered and the solid (4.0 g of 95% pure pyridone carboxylic acid) was further purified by recrystallization from 50% acetic acid (3.5 g, 63.5% yield). 1H NMR ($d_6$ - DMSO) $\delta 10.65$ (bs,2H), 7.45 (d,J=7Hz,1H), 6.8(d,J=1.5Hz,1H), 6.55(dd,J=1.5,7Hz,1H).

Calc. for $C_6H_5NO_3$: C, 51.8; H, 3.6; N, 10.07. Found C, 51.80H, 3.69; N, 9.96.

EXAMPLES 2-3

Using the following substituted isonicotinic acids following the procedure of Example 1, the corresponding substituted 2-hydroxyisonicotinic acids are prepared.

| Example | Acid |
| --- | --- |
| 2 | 3-bromoisonicotinic acid |
| 3 | 3,5,6-trifluoroisonicotinic acid |

EXAMPLE 4

This Example is directed to the preparation of 5-hydroxypicolinic acid (2-hydroxypyridine-6-carboxylic acid).

Picolinic acid (5 g). 6 g KOH and 50 mL water were cooled to $0°$ C. and fluorinated for approximately 3 hours with a 10% $F_2$ in $N_2$ gas mixture. Concentrated HCl was added until the pH was less than 3 and the mixture allowed to stir overnight. Filtration gave 3.3 g yellow-brown solid which was purified by recrystallization from acetic acid (2.9 g, 51% yield). 1H NMR ($d_6$-DMSO) $\delta 7.58$ (d,J=9Hz,1H), 7.02 (d,J=7Hz, 1H). 6.68 (d,J=9Hz,1H). Calc. for $C_6H_5NO_3$ C, 51.80; H, 3.60; N, 10.07. Found; C, 51.34; H, 3.90; N, 10.06.

EXAMPLE 5

Using 3-bromopicolinic acid and following the procedure of Example 4 the corresponding substituted 2-hydroxypicolinic acid is prepared.

EXAMPLE 6

This Example is directed to the preparation of 2- and 6-hydroxynicotinic acids

Nicotonic acid (5 g) was dissolved in 50 mL water containing 5% KOH. This was fluorinated at 0 °C. as in Example 1 with a 10:90 $F_2/N_2$ mixture (total gas flow 100 cc/min) for 3.5 hours. The contents of the reactor were acidified with 5 mL conc. HCl and refluxed for 1 hour. After cooling, the yellow product was filtered and dried. NMR analysis indicated that this was a mixture of 2- and 6-hydroxynicotinic acids (4.2 g, 73%).

EXAMPLE 7-8

Using the following substituted nicotinic acids and following the procedure of Example 6, the corresponding substituted 2-hydroxynicotinic acids are prepared.

| Example | Acid |
|---|---|
| 7 | 5-bromonicotinic acid |
| 8 | 5,6-dichloronicotinic acid |

EXAMPLE 9

2-Hydroxypyridine-5,6-dicarboxylic acid is prepared by reacting 2 3-pyridinedicarboxylic acid according to Example 1.

EXAMPLE 10

2-Hydroxypyridine-4,5,6-tricarboxylic acid is prepared by reacting 2,3,4-pyridinetricarboxylic acid according to Example 1.

EXAMPLE 11

Methyl 1,6-dihydro-6-oxo-pyridine-4-carboxylate is prepared by reacting methyl isonicotinate according to Example 12.

EXAMPLE 12

This Example is directed to the preparation of dimethyl 1,6-dihydro-6-oxo-pyridine-2,3-dicarboxylate.

A solution of 3.0 g (15.4 mol) dimethyl pyridine-2,3-dicarboxylate in 30 mL 2:1 acetonitrile water mixture was cooled to 0° C. $F_2$ (11 cc/min) diluted with $N_2$ (80 cc/min) was bubbled in subsurface for 20 min (total $F_2$, 8.8 mmol). After flushing the system with $N_2$ for 30 min at room temperature, the solution was refluxed for 2 hours. Solvent was removed under vacuum to give a solid which was redissolved in dichloromethane The dichloromethane solution was washed with brine and dried (MgSO$_4$). Evaporation of the solvent gave a yellow powder which was recrystallized from toluene, affording 1.05 g (56%) white needles mp 162°-163° C. (lit. 59°-161° C.). This material was converted into the corresponding diacid in 90% yield by refluxing in aqueous 5% NaOH for 3 hours (mp 248° C.); 1H NMR (DMSO-d$_6$) $\delta$9.9 (bs, 3H), 7.9 (d,J=10Hz,1H), 6.5 (d,J=10 HZ, 1H);

Anal. Calc for $C_7H_5NO_5$:C, 45.91; H, 2.76; N, 7.65; Found; C, 45.64; H, 2.81; N, 7.38.

EXAMPLE 13

This Example is directed to the preparation of dimethyl 1,6-dihydro-6-oxo-pyridine-2,5-dicarboxylate.

In a manner similar to that described in Example dimethyl pyridine-2,5-dicarboxylate was fluorinated with $F_2$ in $N_2$ at 30° C. using a 70:20 acetonitrile-water solvent system. Removal of solvent under vacuum left a residue from which dimethyl 2-hydroxypyridine-2,5dicarboxylate was obtained (1H NMR (CDCl3)) $\delta$8.2 (d, J=8 Hz, 1 H), 7.2 (d,J=8 Hz,1 H) and 3.9 (two singlets, 3 H each); IR (KBr) 3300-2600, 1740, 1655, 1440, 1300 1145, 1070, 760 cm-1.

EXAMPLE 14

Using 5-fluoro dimethyl pyridine-2,5-dicarboxylate and following the procedure of Example 13, the corresponding 6-hydroxy compound is prepared.

EXAMPLE 15

2-hydroxy-3-quinolinecarboxylic acid is prepared by reacting 3-quinolinecarboxylic acid according to Example 1.

EXAMPLE 16

2-hydroxy-3,4-quinolinedicarboxylic acid is prepared by reacting 3,4-quinolinedicarboxylic acid according to Example 1.

EXAMPLE 17

2-hydroxy-3,4,5-quinolinetricarboxylic acid is prepared by reacting 3,4,5-quinolinetricarboxylic acid to Example 1.

EXAMPLE 18

2-hydroxy-3,4,5,6-quinolinetetracarboxylic acid is prepared by reacting 3,4,5,6-quinolinetetracarboxylic acid according to Example 1.

EXAMPLE 19

This Example is directed to the preparation of methyl 2-hydroxyquinoline-4-carboxylate.

Methyl quinoline-4-carboxylate (4.3 g) was dissolved in 50 mL of a 2:1 CH$_3$CN-H$_2$O mixture. Fluorine diluted with $N_2$ ($F_2$ at 8 cc/min; $N_2$ at 80 cc/min) was then bubbled into the solution at room temperature for 38 min (total $F_2$,11.5 mmol). The mixture was cooled in an ice bath and the product filtered. The filter cake was washed twice with 15 mL cold solvent mixture. After drying, the Product weighed 1.77 g (81% based on $F_2$ added) and had mp 249°-252° C. NMR (DMSO-d$_6$); $\delta$8.02 (d, 1 H), 7.1-7.65 (3 H), 6.83 (s, 1H), 3.90 (s, 3 H), 3.3 (s, 1 H); IR (Nujol) 1732 and 1680 cm$^{-1}$.

EXAMPLE 20-24

Using the following substituted esters and following the procedure of Example 19, the corresponding substituted 2-hydroxy compounds are prepared.

| Example | Ester |
|---|---|
| 20 | 3-bromo methyl quinoline-4-carboxylate |
| 21 | 3,5-dichloro methyl quinoline-4-carboxylate |
| 22 | 3,5,6-trifluoro methyl quinoline-4-carboxylate |
| 23 | 3,5,6,7-tetrabromo methyl quinoline-4-carboxylate |
| 24 | 3,5,6,7,8-pentachloro methyl quinoline-4-carboxylate |

Having described the invention in detail and by reference to preferred embodiments thereof, it will be apparent that modifications and variations are possible without departing from the scope of the invention defined in the appended claims.

What is claimed is:

1. A process for the preparation of hydroxy-pyridine based compounds comprising the step of;

in water, reacting a pyridine based compound with the proviso that the second position on the nitrogen ring is unsubstituted and the fourth position on the nitrogen ring is not substituted with halogen and the sixth position on the nitrogen ring is unsubstituted or substituted, with elemental fluorine at a temperature of about $-25°$ to about $+30°$ C. for a time sufficient to form a 2-hydroxypyridine based compound.

2. The process of claim 1 wherein said hydroxypyridine based compound has the formula

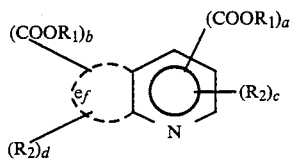

wherein $R_1$ is hydrogen, methyl, or ethyl; a and b are the same or different and the sum of a and b ranges from 1 to 6; $R_2$ is fluorine, chlorine, bromine or iodine; c and d are the same or different and the sum of c and d ranges from 0 to 5; $a+b+c+d \leq 6$; e represents the atoms necessary to form a six carbon ring; f is the number of additional six carbon rings and is 0 or 1; with the proviso that when $R_1$ is hydrogen, an alkali metal hydroxide is added to the water prior to said reaction and when $R_1$ is methyl or ethyl, a water-miscible organic solvent is added to the water prior to said reaction and forms a 2-hydroxypyridine based compound of the formula

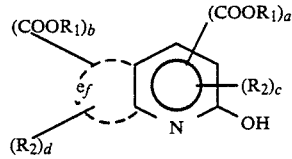

3. The process of claim 1 wherein said reaction is conducted at a temperature of about 0° to about +30° C.

4. The process of claim 2 wherein said $R_1$ is hydrogen.

5. The process of claim 2 wherein said $R_1$ is methyl.

6. The process of claim 2 wherein said $R_1$ is ethyl.

7. The process of claim 1 wherein said elemental fluorine is diluted with nitrogen.

8. The process of claim 2 wherein said water-miscible organic solvent is acetonitrile.

9. The process of claim 2 wherein said alkali hydroxide is potassium hydroxide.

10. The process of claim 2 wherein said alkali metal hydroxide is sodium hydroxide.

11. The process of claim 2 wherein $f=0$ and the sixth position on the nitrogen ring is substituted.

12. The process of claim 2 wherein the sum of a and b is 2.

13. The process of claim 2 wherein said pyridine compound is isonicotinic acid.

14. The process of claim 11 wherein said a is 1, said $R_1$ is hydrogen, said sixth position on the nitrogen ring is substituted with said COOH, and said c is 0.

15. The process of claim 2 wherein said pyridine compound is nicotinic acid.

16. The process of claim 11 wherein said a is 2, said $R_1$ is methyl, said fifth and sixth positions on the nitrogen ring are substituted with said $COOCH_3$, and said c is 0.

17. The process of claim 11 wherein said a is 2, said $R_1$ is methyl, said third and sixth positions on the nitrogen ring are substituted with said $COOCH_3$, and said c is 0.

18. The process of claim 2 wherein said pyridine compound is dimethyl pyridine-3,5-dicarboxylate.

19. The process of claim 2 wherein said pyridine compound is methylquinoline-4-carboxylate.

20. The process of claim 2 wherein said pyridine compound is 3-bromoisonicotinic acid.

* * * * *